United States Patent
Shang et al.

(10) Patent No.: US 8,370,975 B2
(45) Date of Patent: Feb. 12, 2013

(54) MOVABLE EXAMINATION BED

(75) Inventors: Hong Shang, Shanghai (CN); Jin Xiao, Shanghai (CN)

(73) Assignee: Siemens Aktiengesellschaft, München (DE)

( * ) Notice: Subject to any disclaimer, the term of this patent is extended or adjusted under 35 U.S.C. 154(b) by 38 days.

(21) Appl. No.: 12/978,900

(22) Filed: Dec. 27, 2010

(65) Prior Publication Data

US 2011/0179570 A1    Jul. 28, 2011

(30) Foreign Application Priority Data

Dec. 29, 2009    (CN) .......................... 2009 2 0351279

(51) Int. Cl.
*A61G 31/00*    (2006.01)
(52) U.S. Cl. .............................................. 5/600; 5/601
(58) Field of Classification Search .............. 5/600–601, 5/613, 616
See application file for complete search history.

(56) References Cited

U.S. PATENT DOCUMENTS

| | | | | |
|---|---|---|---|---|
| 4,626,813 | A | * | 12/1986 | Koga et al. ...................... 335/278 |
| 5,754,997 | A | * | 5/1998 | Lussi et al. ......................... 5/618 |
| 6,769,145 | B1 | * | 8/2004 | Pfeuffer et al. .................... 5/601 |

* cited by examiner

*Primary Examiner* — Frederick Conley
(74) *Attorney, Agent, or Firm* — Lempia Summerfield Katz LLC

(57) ABSTRACT

The present embodiments provide a movable examination bed that includes a movable platform for supporting an object to be examined, a supporting body connected to the movable platform from below and used for supporting the movable platform, and a guide rail arranged underneath the movable platform. The examination bed also includes a transport mechanism that drives the supporting body such that the supporting body moves on the guide rail. The examination bed includes a connection mechanism securely connected to the transport mechanism, an electromagnet fixed to the connection mechanism and operable to magnetically attract the supporting body, and a controller operable to control the magnetic attraction between the electromagnet and the supporting body. The examination bed is operable to rapidly separate the movable platform from the transport mechanism in case of an emergency and return the movable platform to an original position after the emergency situation is over.

8 Claims, 2 Drawing Sheets

MOVABLE EXAMINATION BED

This application claims the benefit of CN 200920351279.2, filed Dec. 29, 2009.

BACKGROUND

The present embodiments relate to a movable examination bed.

Emergency situations are often encountered during an examination made on an object to be examined using an examination bed. For instance, emergency situations such as, for example, power failure, having a patient's body part collide with or squeezed by diagnostic equipment, or a patient suddenly feeling discomfort may occur during the examination of patients using medical diagnostic equipment such as a Computed Tomographic (CT) machine. The medical diagnostic equipment may be turned off, and a movable platform of an examination bed may be manually and quickly pulled out, so as to quickly release the patient from the medical diagnostic equipment. When a previous operation needs to be continued after an emergency situation is over, the movable platform may be returned to the position where the movable platform was located before the occurrence of the emergency. With regard to a CT machine, two technical solutions may be adopted to solve the problems mentioned above.

The first technical solution is accomplished by installing an encoder on an examination bed. Currently, the available encoders include relative encoders and absolute encoders; relative encoders do not have a built-in power supply inside, so that when the CT machine is turned off, coordinate system data of the relative encoders no longer exist. Therefore, the relative encoders also require additional reference points to be set to be approximately re-positioned. The absolute encoders include a built-in power supply inside, so that when the CT machine is turned off, coordinate positions of the absolute encoders may still be recorded. Thus, the absolute encoders achieve high precision positioning, but costs are much higher than that of the relative encoders.

The second technical solution is accomplished by arranging a permanent magnet on a transport mechanism of an examination bed for a CT machine. Magnetic attraction may occur between the permanent magnet and a supporting body of the movable platform of the examination bed. The transport mechanism is operable to drive the movable platform such that the movable platform runs to the diagnostic region. When one of the emergency situations mentioned above occurs, the CT machine is turned off, the transport mechanism is separated from the movable platform by using an additionally arranged mechanical lever mechanism, and the movable platform is quickly pulled out. At this time, the positions of the transport mechanism and the permanent magnet thereon remain fixed. When the emergency situation is over, the movable platform is manually controlled until the supporting body is magnetically attracted onto the permanent magnet again. The movable platform is also returned to the position where the movable platform was located before the occurrence of the emergency situation.

In the second technical solution, two permanent magnets may be used. Therefore, the space occupied by the permanent magnets is large, and the costs are high. The permanent magnets also bring about some problems with transportation and installation, while the additional mechanical lever mechanism further increases the operation costs.

SUMMARY AND DESCRIPTION

The present embodiments may obviate one or more of the drawbacks or limitations in the art. For example, a movable examination bed that allows for quickly separating a movable platform on the examination bed from a transport mechanism in a case of emergency and returning the movable platform to the position where the movable platform was located before the separation, after the emergency is over, may be provided.

According to an embodiment of the movable examination bed, the examination bed includes a movable platform operable to support an object to be examined. The examination bed also includes a supporting body securely connected to the movable platform from below and at least one guide rail operable to support the supporting body to move therealong. The examination bed includes a transport mechanism for driving the supporting body, such that the support body moves on the at least one guide rail, a connection mechanism fixed to the transport mechanism, and an electromagnet fixed to the connection mechanism. The electromagnet is operable to magnetically attract the supporting body. The examination bed also includes a controller, where the controller is operable to control the magnetic attraction between the electromagnet and the supporting body.

In one embodiment of the movable examination bed, the controller includes a control button that is operable to control the magnetization and demagnetization of the electromagnet independently from the operation of the transport mechanism.

According to another embodiment of the movable examination bed, the controller includes a permanent magnet mounted at a central position on the electromagnet, at which no coil is arranged.

According to yet another embodiment of the movable examination bed, the connection mechanism slides on the at least one guide rail by a sliding device.

According to the examination bed of the present embodiment, when the electromagnet is magnetized (e.g., turned on), the magnetic attraction between the electromagnet and the supporting body supporting the movable platform may drive the movable platform, such that the movable platform moves on the guide rail, so as to move the object to be examined to the examination region; when the electromagnet is demagnetized (e.g., turned off), the electromagnet may be separated from the supporting body, and thus the operator of the examination bed may manually and quickly pull out the movable platform and the object to be examined thereon in a case of emergency. Since, when an emergency occurs, the operation of the transport mechanism stops, and the position of the electromagnet remains fixed, after the emergency is over and before the transport mechanism runs, the movable platform may be returned to the position where the movable platform was located before the occurrence of the emergency using the controller that works independently from the transport mechanism.

The controller may include a control button for controlling the magnetization and demagnetization of the electromagnet, the control button being operable to work independently from a drive motor of the transport mechanism. When the emergency is over, the operator may first use the control button to magnetize the electromagnet and make the movable platform move forward until a magnetic attraction occurs between the movable platform and the electromagnet so as to fix the movable platform and the electromagnet together. Thus, the movable platform may return to the position where the movable platform was located before the occurrence of the emergency.

In one embodiment, the controller may also include a permanent magnet arranged at a central position on the electromagnet, at which no coil is arranged. The permanent magnet has a weak magnetic force, and when an emergency situation occurs, the movable platform may be quickly separated from the electromagnet without making use of a mechanical lever mechanism. When the emergency is over, under the circumstances that the electromagnet is not yet magnetized, the permanent magnet may also achieve a pre-attraction between the movable platform and the electromagnet, such that the movable platform returns to the position where the movable platform was located before the occurrence of the emergency.

One end of the connection mechanism is securely connected with the transport mechanism, and the other end of the connection mechanism is slidably connected with the guide rail. The electromagnet on the connection mechanism may be located at a stable position, and no displacement occurs during the movement.

As compared with the prior art, the space occupied by the electromagnet used in the movable examination bed of the present embodiments is small, and costs are lower than that of a permanent magnet. Therefore, no burden will be placed on the transportation and installation of the electromagnet. The operation of the electromagnet is more convenient, and without the need of an additional mechanical mechanism, the movable platform may be separated from the transport mechanism. Thus, the movable platform of the examination bed may be accurately returned to the position where the movable platform was located before the occurrence of the emergency, after the emergency is over, making it possible for the examination to proceed.

DETAILED DESCRIPTION OF THE DRAWINGS

Figure 1:
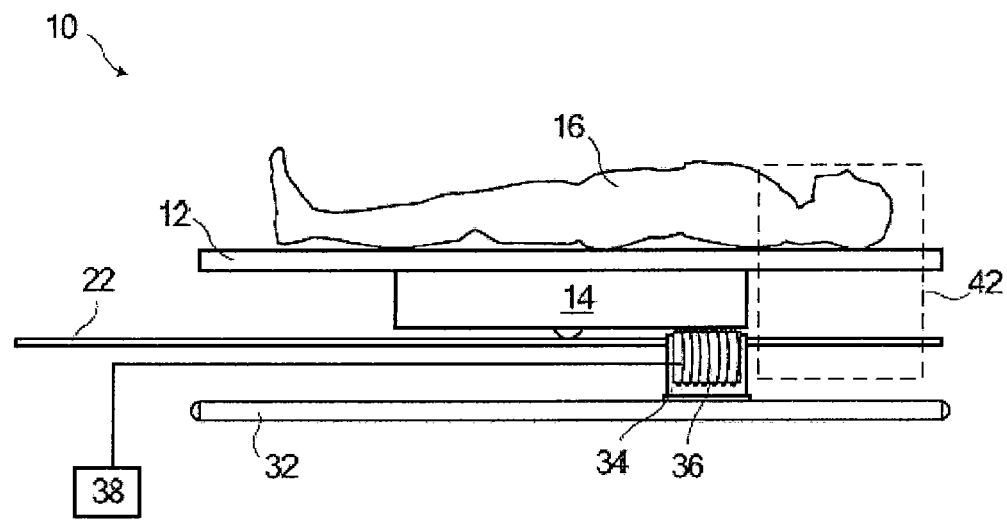
FIG. 1 is a schematic view of a working state of one embodiment of a movable examination bed.

In order to understand more clearly the technical features, objects, and effects of the present embodiments, the same reference numerals are used in each view to represent parts with the same structure or with similar structure but the same function. The word "a" referred to in the present description is not limited to the case of one, but also includes the cases of more than one. The word "on" referred to in the present description not only includes directly on, but also includes the cases of indirectly on via a third component.

FIG. 1 shows a movable examination bed 10 that includes a movable platform 12, a supporting body 14, and at least one guide rail 22. An object to be examined such as, for example, a patient 16 for examination may be placed on the movable platform 12. The supporting body 14 is securely connected to the movable platform 12 from below for supporting the movable platform 12. The supporting body 14 may move on the guide rail 22, such that the supporting body 14 drives the movable platform 12.

The movable examination bed 10 also includes a transport mechanism 32, a connection mechanism 34, and an electromagnet 36. The connection mechanism 34 is fixed to the transport mechanism 32. For example, one end (e.g., a lower end) of the connection mechanism 34 is fixed to the transport mechanism 32, while the other end of the connection mechanism 34 may slide on the guide rail 22. The electromagnet 36 is securely connected to the connection mechanism 34 and may magnetically attract the supporting body 14. The movable examination bed 10 includes a controller, the controller being operable to control the attraction between the electromagnet 36 and the supporting body 14 independently from the operation of the transport mechanism 32.

Figure 2:
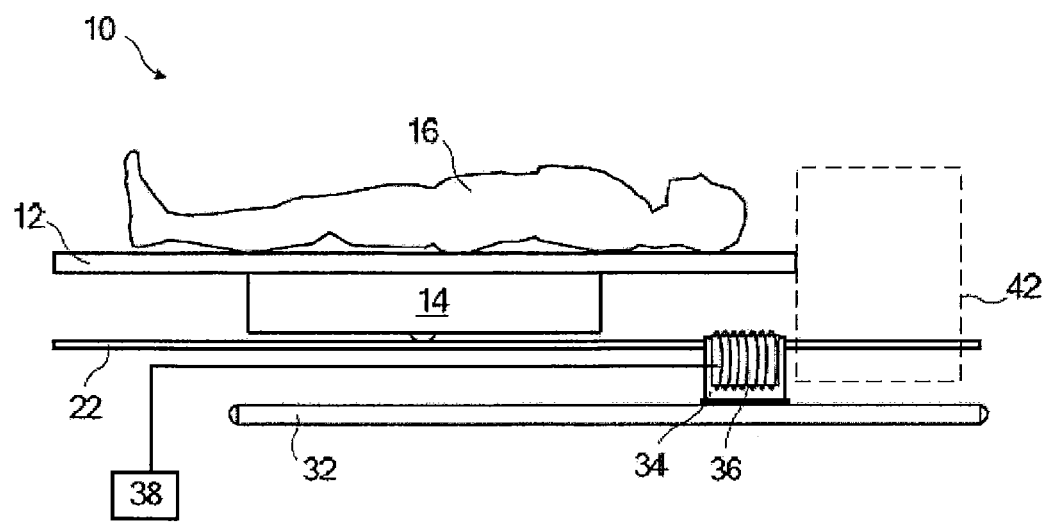
FIG. 2 is a schematic view of another working state of the movable examination bed shown in FIG. 1.

FIGS. 1 and 2 show a first embodiment of the movable examination bed 10. The controller includes a control button 38, and the control button 38 controls the magnetization or demagnetization of the electromagnet 36. The control by the control button 38 of the electromagnet 36 may be independent from the operation of the transport mechanism 32; for example, a power supply of the control button 38 may be independent from the working power supply to the transport mechanism 32. The control button 38 may achieve the magnetization or demagnetization of the electromagnet 36 even when the transport mechanism 32 is turned off.

In FIG. 1, the electromagnet 36 is in a state of being turned on, and the electromagnet 36 attracts onto the supporting body 14 by a magnetic force. Thus, the transport mechanism 32 may drive the supporting body 14 and the movable platform 12 to move towards a region to be examined 42. When an emergency incident occurs (e.g., a power failure with a body part of a patient colliding with or squeezed by the examination equipment, and the patient suddenly feeling discomfort), the power supply of the transport mechanism 32 may be switched off, and the control button 38 may be pressed down to demagnetize the electromagnet 36, so as to break the attraction between the supporting body 14 and the electromagnet 36. At this time, the operator may manually pull out the movable platform 12 to the position shown in FIG. 2.

After the emergency is over, the operator operates the control button 38 once again to magnetize the electromagnet 36, while the transport mechanism 32 is kept in a static state. The position of the electromagnet 36 on the transport mechanism 32 is constantly kept unchanged during this process. The operator continues to push the movable platform 12 along the guide rail 22 towards the region to be examined 42, and the supporting body 14 moves together with the movable platform 12. When the supporting body 14 moves to the position where the supporting body 14 was located before the occurrence of the emergency incident, a magnetic attraction force again occurs between the electromagnet 36 and the supporting body 14. At this time, the transport mechanism 32 runs again, so that the transport mechanism 32 drives the movable platform 12 to continue to move towards the region to be examined 42 to continue the operation as before the occurrence of the emergency incident.

Figure 3:
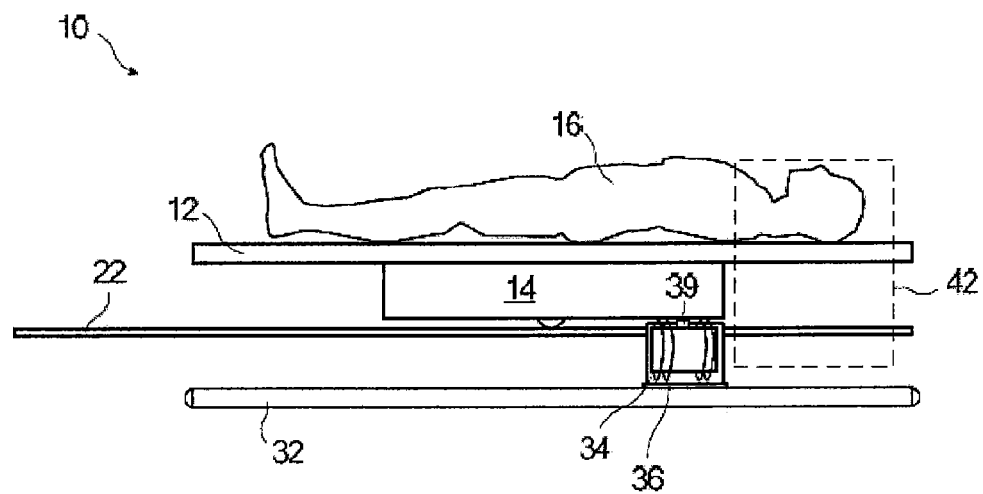
FIG. 3 is a schematic view of a working state of another embodiment of a movable examination bed.
Figure 4:
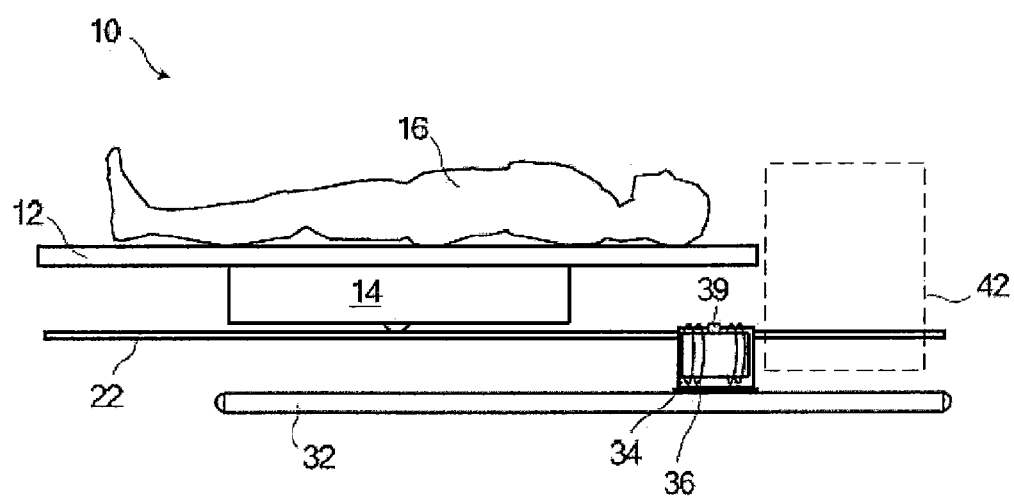
FIG. 4 is a schematic view of another working state of the movable examination bed shown in FIG. 3.

FIGS. 3 and 4 show a second embodiment of the movable examination bed 10. The controller includes a permanent magnet 39, the permanent magnet 39 being arranged at a central part on the electromagnet 36, at which no coil is arranged. The permanent magnet 39 has a weaker magnetic force and the magnetic force produced by the permanent magnet 39 does not interfere with the magnetic force that is produced by the electromagnet 36. Under the circumstances that the electromagnet 36 is turned on to become magnetized, the permanent magnet 39 and the electromagnet 36 do not influence each other.

Referring to FIG. 3, when the electromagnet 36 is turned on, the electromagnet 36 attracts the supporting body 14 by a magnetic force. Therefore, the transport mechanism 32 may drive the supporting body 14 and the movable platform 12, such that the supporting body 14 and the movable platform 12 move towards the region to be examined 42. When the emergency incident occurs, a power supply of the entire examination bed 10 may be turned off. At this time, the transport mechanism 32 no longer moves, and the electromagnet 36 is demagnetized, so as to break the attraction between the supporting body 14 and the electromagnet 36; the operator may manually pull out the movable platform 12 to the state shown in FIG. 4.

After the emergency is over, the operator pushes the movable platform 12 along the guide rail 22 to move the movable platform 12 and the supporting body 14 towards the region to be examined 42. When the supporting body 14 moves to the position where the supporting body 14 was located before the occurrence of the emergency incident, a pre-attraction force occurs between the permanent magnet 39 and the supporting body 14. Since the positions of the transport mechanism 32, the electromagnet 36, and the permanent magnet 39 are unchanged during the process, the supporting body 14 may return to the position where the supporting body 14 was located before the occurrence of the emergency incident. The electromagnet 36 may be magnetized again, and the transport mechanism 32 may be actuated. The transport mechanism 32 may thus drive the movable platform 12, such that the movable platform 12 continues to move toward the region to be examined 42, and the operation is continued as before the occurrence of the emergent accident.

In other embodiments of the movable examination bed 10, the controller may include both the control button 38 as shown in FIG. 1 and the permanent magnet 39 as shown in FIG. 3. Therefore, in one aspect, the movable examination bed 10 is mainly dependent on the electromagnet 36 to achieve the accurate restoration of the movable platform 12 and the supporting body 14 in the event that the control button 38 is not turned off; in another aspect, the permanent magnet may still be used to achieve the pre-attraction between the supporting body 14 and the electromagnet 36, even in the emergency case that the control button 38 is also turned off. Thus, the movable platform 12 is operable to return to the position where the movable platform 12 was located before the occurrence of the emergency. In this embodiment, the operation and control modes of the control button 38 and the permanent magnet 39 are similar to that in the first and second embodiments, which are not described redundantly herein.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A movable examination bed comprising:
   a movable platform that supports an object to be examined;
   a supporting body connected to the movable platform from below;
   a guide rail operable to support the supporting body, such that the supporting body moves along the guide rail;
   a transport mechanism that drives the supporting body such that the supporting body moves on the guide rail;
   a connection mechanism that is fixed to the transport mechanism;
   an electromagnet fixed to the connection mechanism, the electromagnet being operable to magnetically attract the supporting body; and
   a controller that is operable to control the magnetic attraction between the electromagnet and the supporting body.

2. The movable examination bed as claimed in claim 1, wherein the controller comprises a control button that controls the magnetization and demagnetization of the electromagnet independently from the operation of the transport mechanism.

3. The movable examination bed as claimed in claim 2, wherein the controller further comprises a permanent magnet mounted on the electromagnet.

4. The movable examination bed as claimed in claim 3, wherein the permanent magnet is located at a position on the electromagnet, at which no coil is arranged.

5. The movable examination bed as claimed in claim 1, wherein the controller comprises a permanent magnet mounted on the electromagnet.

6. The movable examination bed as claimed in claim 5, wherein the permanent magnet is located at a position on the electromagnet, at which no coil is arranged.

7. The movable examination bed as claimed in claim 6, wherein the permanent magnet is located at a central position on the electromagnet at which no coil is arranged.

8. The movable examination bed as claimed in claim 1, wherein the connection mechanism is operable to slide on the guide rail.

* * * * *